United States Patent [19]

Gennari

[11] Patent Number: 4,673,534
[45] Date of Patent: Jun. 16, 1987

[54] CARNITINE SALTS PARTICULARLY SUITABLE FOR ORAL USE

[75] Inventor: Federico Gennari, Truccazzano, Italy

[73] Assignee: Bioresearch Spa, Liscate, Italy

[21] Appl. No.: 878,698

[22] Filed: Jun. 26, 1986

[30] Foreign Application Priority Data

Jul. 5, 1985 [IT] Italy ................ 21445 A/85

[51] Int. Cl.$^4$ .................................. C07C 143/34
[52] U.S. Cl. ................................. 260/501.12
[58] Field of Search .................... 260/501.12; 514/561

[56] References Cited

U.S. PATENT DOCUMENTS

| 2,781,380 | 2/1957 | Mannheimer | 260/501.12 |
| 4,000,091 | 12/1976 | Wentler | 260/501.12 |
| 4,000,092 | 12/1976 | Wentler | 260/501.12 |
| 4,259,191 | 3/1981 | Wagner | 260/501.12 |
| 4,383,929 | 5/1983 | Bertocchio | 260/501.12 |

FOREIGN PATENT DOCUMENTS

| 2038163 | 2/1971 | Fed. Rep. of Germany | 260/501.12 |
| 0225990 | 8/1985 | Fed. Rep. of Germany | 260/501.12 |

*Primary Examiner*—Paul J. Killos
*Attorney, Agent, or Firm*—Stevens, Davis, Miller & Mosher

[57] ABSTRACT

New carnitine salts with sulphonic acids, of general formula:

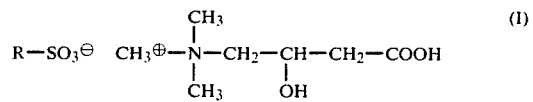

in which R is a linear or branched alkyl chain of 8 to 18 carbon atoms, and which are particularly suitable for oral use.

Said salts are prepared by the following stages:
(a) preparing an aqueous solution of carnitine inner salt;
(b) preparing an aqueous solution of a sulphonic acid of formula RSO$_3$H in which R has the aforesaid meaning;
(c) reacting the carnitine inner salt with the sulphonic acid in aqueous solution, and recovering the salt produced by drying the solution.

10 Claims, No Drawings

CARNITINE SALTS PARTICULARLY SUITABLE FOR ORAL USE

This invention relates to new carnitine salts with sulphonic acids, of general formula:

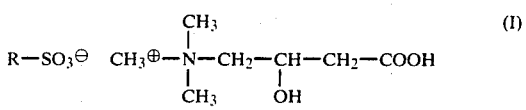

in which R is a linear or branched alkyl chain of 8 to 18 carbon atoms.

The invention also relates to the process for obtaining said salts and to the pharmaceutical preparations containing them as active principle either alone or together with excipients and auxiliary agents normally used in pharmaceutics.

Carnitine is a physiological compound found in all mammal tissues, with particularly high concentrations in the skeletal and cardiac muscle.

This product, currently available commercially as the hydrochloride, is applied clinically in skeletal myopathy and myopathy of the myocardium.

The carnitine salts of the present invention have a considerably greater bioavailability than the currently available known salts. In particular, the salts according to the invention have the advantage of greater absorption into the gastro-enteric tract and are therefore particularly suitable for oral use.

They are soluble in a large number of polar solvents or solvents of medium polarity, ranging from water to alcohols and alcohol-chloroform mixtures.

The process for preparing the carnitine salts according to the present invention is characterised by the following stages:
(a) preparing an aqueous solution of carnitine inner salt;
(b) preparing an aqueous solution of a sulphonic acid of formula $RSO_3H$ in which R is a linear or branched alkyl chain of 8 to 18 carbon atoms;
(c) reacting the carnitine inner salt with the sulphonic acid in aqueous solution, and recovering the salt produced by drying the solution.

These and further characteristics of the process according to the invention, and of the products obtained and relative pharmaceutical formulations, will be more apparent from the description given herinafter of preferred embodiments of the invention and of trials involving the administration of the products obtained.

Stage (a) is carried out by dissolving commercial carnitine hydrochloride in water to concentrations variable between 5% and 25% w/v and eliminating the chloride ion by passage through a column containing a weak anion exchanger in $OH^-$ form in a quantity of between 1 and 10 liters of resin per mole of carnitine, and preferably 2 liters of resin per mole of carnitine.

The resins preferably used are:
Amberlite: IRA 93
Dowex: MWA 1
Duolite: ES 366
ICC: AFP 329

This treatment results in a solution of carnitine inner salt in a concentration of between 3% and 20%, and preferably 15% w/v.

Stage (b) is carried out by dissolving the sodium salt of the required sulphonic acid in water at a temperature of between 20° C. and 80° C., according to its solubility in water, to a concentration of between 5% and 30% w/v, then eliminating the sodium ion by passage through a column containing a strongly acid cation exchanger in $H^+$ form in a quantity of between 1 and 10 liters of resin per mole of sulphonic acid, and preferably 2 liters of resin per mole of sulphonic acid.

The resins preferably used are:
Amberlite: IR 120
Dowex: 550 W-X8
Duolite: C 20

The sulphonic acid sodium salts $RSO_3Na$ in which R is a linear or branched alkyl chain of 8 to 18 carbon atoms are easily prepared from the corresponding bromides by reaction with sodium sulphite in accordance with the equation:

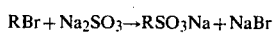

in which R is as heretofore defined.

The procedure is as already described by the applicant in patent application No. 20940 A/84 (Italy).

This treatment results in a solution of the required sulphonic acid in a concentration of between 3% and 25% w/v, and preferably 20%.

Stage (c) is carried out by mixing together equimolar solutions from stage (a) and stage (b), under agitation at ambient temperature for a time of between 10 and 30 minutes, then drying the resultant solution by lyophilisation or spray-drying, or other known drying techniques for pharmaceutical products.

The absorption of these new carnitine salts compared with the comparison hydrochloride was studied by evaluating the plasmatic concentrations of the active principle after intraduodenal and oral administration of the products.

(1) Intraduodenal Administration

This trial was conducted on male Sprague-Dawley rats of average weight 272 grams, under fasting from the previous day.

The animals were operated on under ether anesthesia to expose a portion of the proximal jejunum, into which the drugs were injected suspended in 0.2% Methocel.

The suspensions were administered in a quantity of 2 ml/kg, the resultant dose being 100 mg of active principle per kg of body weight.

Each product was administered to four animals, two of which were sacrificed 10 minutes after administration and the other two 20 minutes after administration.

At each of these times both the portal blood and the aortic blood were withdrawn. The basal samples were obtained from rats which had not been operated on. The blood was withdrawn with a syringe containing 10% w/v EDTA $K_2$ (20 $\mu$l/ml blood) and immediately centrifuged. The supernatant plasma was analysed by the colorimetric-enzymatic method of D. J. Pearson et al. (Methods of Enzymatic Analysis, Bergmeyer H. V. Ed., Academic Press 1974, page 1762), after filtering through Centrifree Amicon.

The O.D. values enabled the content of the unknown samples to be obtained by comparison with the O.D. values obtained from solutions containing a known amount of active principle in plasma.

(2) Oral Administration

The oral trial was carried out on 6 male Sprague-Dawley rats of average weight 205 grams, under fasting from the previous evening.

The animals, 3 per product, were treated orally with 200 mg of active principle per kg of body weight.

Blood was withdrawn from the caudal vein of each animal 15, 30, 60, 120, 180 and 360 minutes after administration.

The tested products corresponded to the following symbols:

| | |
|---|---|
| BR 2735 | L-carnitine hydrochloride (comparison) |
| BR 730 | L-carnitine octanesulphonate |
| BR 731 | L-carnitine decanesulphonate |
| BR 732 | L-carnitine dodecanesulphonate |
| BR 733 | L-carnitine tetradecanesulphonate |
| BR 734 | L-carnitine hexadecanesulphonate |
| BR 735 | L-carnitine octadecanesulphonate |

Table 1 shows the active principle concentrations in the portal plasma and aortic plasma of the rats treated by intraduodenal administration with the salts of the present invention, compared with carnitine hydrochloride. These concentrations are expressed in nmoles of active principle per ml of plasma.

TABLE 1

| | Intraduodenal administration | | |
|---|---|---|---|
| Product | Time (min) | Portal plasma | Aortic plasma |
| BR 2735 | 10 | 235 | 50.6 |
| BR 2735 | 20 | 85 | 40.8 |
| BR 730 | 10 | 1120 | 453 |
| BR 730 | 20 | 980 | 417 |
| BR 731 | 10 | 1250 | 470 |
| BR 731 | 20 | 1030 | 423 |
| BR 732 | 10 | 1380 | 495 |
| BR 732 | 20 | 1120 | 448 |
| BR 733 | 10 | 1450 | 536 |
| BR 733 | 20 | 1180 | 477 |
| BR 734 | 10 | 1520 | 598 |
| BR 734 | 20 | 1210 | 535 |
| BR 735 | 10 | 1550 | 625 |
| BR 735 | 20 | 1230 | 580 |

From Table 1 it can be seen that for equal administered doses, the new carnitine salts are more greatly absorbed than the currently available hydrochloride (BR 2735).

Table 2 shows the active principle concentrations in the plasma (nmoles/ml of plasma) after oral administration of the new salts of the present invention, compared with carnitine hydrochloride (BR 2735).

TABLE 2

| | Oral administration | | | | | | |
|---|---|---|---|---|---|---|---|
| Time after admin. (min) | BR 2735 | BR 730 | BR 731 | BR 732 | BR 733 | BR 734 | BR 735 |
| 15 | 45 | 92 | 103 | 110 | 113 | 121 | 125 |
| 30 | 58 | 166 | 178 | 181 | 182 | 190 | 193 |
| 60 | 70 | 320 | 351 | 363 | 371 | 368 | 385 |
| 120 | 66 | 211 | 275 | 284 | 292 | 292 | 301 |
| 180 | 58 | 150 | 181 | 185 | 191 | 187 | 203 |
| 360 | 44 | 138 | 143 | 148 | 153 | 155 | 162 |

Again it is apparent that for equal administered doses, the new carnitine salts are more greatly absorbed than the currently available hydrochloride (BR 2735).

The new carnitine salts according to the present invention can be presented in injectable formulations, but more specifically in oral formulations such as tablets, pills, capsules, sustained-release capsules, sustained-release tablets, gastroresistant tablets, sachets, syrups, extemporaneous syrups, sustained-release syrups and other forms normally used in pharmaceutics.

The following examples are described for the purpose of nonlimitative illustration of the preparation process for the new carnitine salts.

EXAMPLE 1

Preparation of L-carnitine octanesulphonate

A column containing 20 liters of Amberlite IRA 93 resin in OH$^-$ form is prepared and carefully activated with 2N NaOH, then washed with distilled water until the eluate is neutral.

Separately, 1.98 kg of commercial L-carnitine hydrochloride are dissolved in 25 liters of distilled water, and the solution is passed through the previously prepared column.

This is then washed with water until carnitine disappears from the eluate.

The carnitine solution is concentrated under vacuum to a volume of 10,8 liters containing 1.61 kg of L-carnitine inner salt. Separately, a second column of Amberlite IR 120 resin in H$^+$ form is prepared and carefully activated with 6N HCl, then washed with distilled water until the eluate is neutral.

2.165 kg of sodium octanesulphonate are dissolved in 50 liters of distilled water at 40° C., and the solution thus obtained is passed through the previously prepared column.

This is washed with 20 liters of distilled water to obtain 70 liters of a solution containing 1.945 kg of octanesulphonic acid.

This solution is concentrated by boiling to 40 liters, and cooled to 20° C.

The carnitine inner salt solution is mixed with the octanesulphonic acid solution at ambient temperature under agitation for 20 minutes, and the homogeneous solution obtained is lyophilised.

In this manner 3.600 kg of a white powder are obtained, showing the following composition on analysis:

L-carnitine: 44.5%
octanesulphonic acid: 54%
$H_2O$: 1.5%

The product is in the form of a white powder soluble in water, methanol, ethanol and 2:1 methanol-chloroform mixtures.

The L-carnitine was determined quantitatively by the aforesaid colorimetric-enzymatic method of Pearson et al.

On thin layer chromatography with a G. Merck alumina support, acetic acid-acetone-methanol-benzene (5+5+20+70) solvent and Dragendorff reagent as detector, the product shows a single spot with Rf=0.20, exactly corresponding to that of carnitine hydrochloride.

Elementary analysis: $C_7H_{15}NO_3 \cdot C_8H_{18}O_3S$

| | N | C | H |
|---|---|---|---|
| Calculated: | 3.94 | 50.67 | 9.36 |
| Found: | 3.87 | 50.21 | 9.18 |

EXAMPLE 2

Preparation of L-carnitine decanesulphonate

The procedure of Example 1 is followed, but using 2.445 kg of sodium decanesulphonate dissolved in 60 liters of distilled water at 40° C.

3.9 kg of a white powder are obtained, showing the following composition on analysis:

L-carnitine: 41.3%
decanesulphonic acid: 56.9%
H$_2$O: 1.8%

The product is in the form of a white powder soluble in water, methanol, ethanol and 2:1 methanol-chloroform mixtures.

On thin layer chromatography in accordance with Example 1, the product shows a single spot with Rf=0.20, exactly corresponding to that of carnitine hydrochloride.

Elementary analysis: C$_7$H$_{15}$NO$_3$.C$_{10}$H$_{22}$O$_3$S

|  | N | C | H |
|---|---|---|---|
| Calculated: | 3.65 | 53.23 | 9.72 |
| Found: | 3.41 | 52.97 | 9.68 |

EXAMPLE 3

Preparation of L-carnitine dodecanesulphonate

The procedure of Example 1 is followed, but using 2.725 kg of sodium dodecanesulphonate dissolved in 100 liters of distilled water at 40° C. 4.2 kg of a white powder are obtained, showing the following composition on analysis:

L-carnitine: 38.4%
dodecanesulphonic acid: 59.6%
H$_2$O: 2%

The product is in the form of a white powder soluble in water, methanol, ethanol and 2:1 methanol-chloroform mixtures.

On thin layer chromatography in accordance with Example 1, the product shows a single spot with RF=0.20, exactly corresponding to that of carnitine hydrochloride.

Elementary analysis: C$_7$H$_{15}$NO$_3$.C$_{12}$H$_{26}$O$_3$S.0.5H$_2$O

|  | N | C | H |
|---|---|---|---|
| Calculated: | 3.33 | 54.26 | 10.06 |
| Found: | 3.42 | 54.11 | 9.87 |

EXAMPLE 4

Preparation of L-carnitine tetradecanesulphonate

The procedure of Example 1 is followed, but using 3 kg of sodium tetradecanesulphonate dissolved in 120 liters of distilled water at 50° C., the column being controlled at this temperature.

Instead of being lyophilised, the final solution is dried in a spray-dryer operating with inlet air at 160° C., the dry product being continuously extracted.

4.5 kg of a white powder are obtained, showing the following composition on analysis:

L-carnitine: 35.8%
tetradecanesulphonic acid: 61.9%
H$_2$O: 2.3%

The product is in the form of a white powder soluble in water, methanol, ethanol and 2:1 methanol-chloroform mixtures.

On thin layer chromatography in accordance with Example 1, the product shows a single spot with Rf=0.20, exactly corresponding to that of carnitine hydrochloride.

Elementary analysis: C$_7$H$_{15}$NO$_3$.C$_{14}$H$_{30}$O$_3$S.0.5H$_2$O

|  | N | C | H |
|---|---|---|---|
| Calculated: | 3.12 | 56.21 | 10.34 |
| Found: | 3.17 | 55.98 | 10.27 |

EXAMPLE 5

Preparation of L-carnitine hexadecanesulphonate

The procedure of Example 1 is followed, but using 3.285 kg of sodium hexadecanesulphonate dissolved in 150 liters of distilled water at 65° C., the column being controlled at this temperature.

4.8 kg of a white powder are obtained, showing the following composition on analysis:

L-carnitine: 33.6%
hexadecanesulphonic acid: 63.8%
H$_2$O: 2.6%

The product is in the form of a white powder relatively little soluble in water, but soluble in methanol, ethanol and 2:1 methanol-chloroform mixtures.

On thin layer chromatography in accordance with Example 1, the product shows a single spot with Rf=0.20, exactly corresponding to that of carnitine hydrochloride.

Elementary analysis: C$_7$H$_{15}$NO$_3$.C$_{16}$H$_{34}$O$_3$S.0.7H$_2$O

|  | N | C | H |
|---|---|---|---|
| Calculated: | 2.91 | 57.5 | 10.58 |
| Found: | 2.88 | 57.1 | 10.61 |

EXAMPLE 6

Preparation of L-carnitine octadecanesulphonate

The procedure of Example 1 is followed, but using 3.565 kg of sodium octadecanesulphonate dissolved in 175 liters of distilled water at 80° C., the column being controlled at this temperature.

5.1 kg of a white powder are obtained, showing the following composition on analysis:

L-carnitine: 31.6%
octadecanesulphonic acid: 65.6%
H$_2$O: 2.8%

The product is in the form of a white powder slightly soluble in water, but very soluble in methanol, ethanol and 1:1 methanol-chloroform mixtures.

On thin layer chromatography in accordance with Example 1, the product shows a single spot with Rf=0.20, exactly corresponding to that of carnitine hydrochloride.

Elementary analysis: C$_7$H$_{15}$NO$_3$.C$_{18}$H$_{38}$O$_3$S.0.8H$_2$O

|  | N | C | H |
|---|---|---|---|
| Calculated: | 2.74 | 58.86 | 10.78 |
| Found: | 2.75 | 58.53 | 10.84 |

EXAMPLE 7

Preparation of gastroresistant tablets (a) A 200 mg tablet contains:

| L-carnitine octadecanesulphonate | 633 mg |
|---|---|
| equivalent to L-carnitine | 200 mg |
| cross-linked sodium | 70 mg |

-continued

| | |
|---|---|
| carboxymethylcellulose microcrystalline cellulose | to make up to 900 mg |
| cellulose acetophthalate | 20 mg |
| diethylphthalate | 6.4 mg |
| silicone resin | 3.6 mg |

(b) A 300 mg tablet contains:

| | |
|---|---|
| L-carnitine hexadecanesulphonate | 893 mg |
| equivalent to L-carnitine | 300 mg |
| cross-linked polyvinylpyrrolidone | 200 mg |
| sodium chloride | 200 mg |
| microcrystalline cellulose | to make up to 1500 mg |
| cellulose acetophthalate | 40 mg |
| diethylphthalate | 12.8 mg |
| silicone resin | 7.2 mg |

(c) A 200 mg tablet contains:

| | |
|---|---|
| L-carnitine dodecanesulphonate | 521 mg |
| equivalent to L-carnitine | 200 mg |
| sodium bicarbonate | 150 mg |
| citric acid | 75 mg |
| cellulose acetophthalate | 20 mg |
| diethylphthalate | 6.4 mg |
| silicone resin | 3.6 mg |

EXAMPLE 8

Preparation of capsules (a) A 200 mg capsule contains:

| | |
|---|---|
| L-carnitine hexadecanesulphonate | 595 mg |
| equivalent to L-carnitine | 200 mg |
| lactose | 200 mg |
| magnesium stearate | 12 mg |

(b) A 200 mg capsule contains:

| | |
|---|---|
| L-carnitine octadecanesulphonate | 633 mg |
| equivalent to L-carnitine | 200 mg |
| mannitol | 100 mg |
| lactose | 100 mg |
| magnesium stearate | 12 mg |

EXAMPLE 9

Preparation of capsules with sugar-coated pellets (a) A 200 mg capsule with sugar-coated pellets contains:

| | |
|---|---|
| L-carnitine tetradecanesulphonate | 559 mg |
| equivalent to L-carnitine | 200 mg |
| sugar-coated pellets | 200 mg |

(b) A 200 mg capsule with sugar-coated pellets contains:

| | |
|---|---|
| L-carnitine octadecanesulphonate | 633 mg |
| equivalent to L-carnitine | 200 mg |
| sugar-coated pellets | 200 mg |

I claim:

1. Carnitine salts with sulphonic acids, characterised by the general formula:

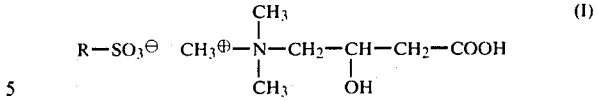

in which R is a linear or branched alkyl chain of 8 to 18 carbon atoms.

2. A process for producing new carnite salts with sulponic acids of general formula:

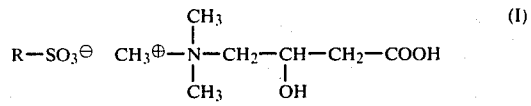

in which R is a linear or branched alkyl chain of 8 to 18 carbon atoms, characterised by the following stages:

(a) preparing an aqueous solution of carnitine inner salt;

(b) preparing an aqueous solution of a sulphonic acid of formula $RSO_3H$ in which R has the aforesaid meaning;

(c) reacting the carnitine inner salt with the sulphonic acid in aqueous solution, and recovering the salt produced by drying the solution.

3. A process as claimed in claim 2, characterised in that said aqueous solution of carnitine inner salt is prepared by dissolving carnitine hydrochloride in water to obtain concentrations of between 5% and 25% w/v, and eliminating the chloride ion by passage through a column containing a weak anion exchanger in $OH^-$ form.

4. A process as claimed in claim 2, characterised in that said aqueous solution of carnitine inner salt is prepared at a concentration of between 3% and 20%, and preferably of 15% w/v.

5. A process as claimed in claim 2, characterised in that said solution of a sulphonic acid is prepared by dissolving the sulphonic acid sodium salt in water at a temperature of between 20° C. and 80° C. to obtain concentrations of between 5% and 30% w/v, and eliminating the sodium ion by passage through a column containing a strongly acidic cation exchanger in $H^+$ form.

6. A process as claimed in claim 2, characterised in that said solution of a sulphonic acid is prepared at a concentration of between 3% and 25%, and preferably of 20% w/v.

7. A process as claimed in claim 2, characterised in that said reaction between carnitine inner salt and sulphonic acid is carried out by mixing together under agitation, at ambient temperature for a time of between 10 and 30 minutes, equimolar solutions of the two reagents prepared in accordance with claims 3 to 6.

8. A process is claimed in claim 2, characterised in that said drying of the solution in order to recover the salt produced is carried out by lyophilisation or spray-drying.

9. Pharmaceutical compositions particularly suitable for oral administration for the treatment of skeletal myopathy and myopathy of the myocardium, comprising at least one compound of general formula (I) as defined in claim 1 as active principle, and a pharmaceutically acceptable carrier.

10. The use of a compound of general formula (I) as defined in claim 1 for the preparation of pharmaceutical products for treating skeletal myopathy and myopathy of the myocardium.

* * * * *